US008318084B2

(12) United States Patent
Johnson et al.

(10) Patent No.: US 8,318,084 B2
(45) Date of Patent: Nov. 27, 2012

(54) METHOD AND DEVICE FOR CLEANING AIR

(75) Inventors: Matthew Stanley Johnson, Lund (SE); Jan Arlemark, Höllviken (SE)

(73) Assignee: Kobenhavns Universitet, Copenhagen (DK)

( * ) Notice: Subject to any disclaimer, the term of this patent is extended or adjusted under 35 U.S.C. 154(b) by 12 days.

(21) Appl. No.: 12/992,708

(22) PCT Filed: May 14, 2009

(86) PCT No.: PCT/EP2009/055849
§ 371 (c)(1), (2), (4) Date: Apr. 1, 2011

(87) PCT Pub. No.: WO2009/138464
PCT Pub. Date: Nov. 19, 2009

(65) Prior Publication Data
US 2011/0171090 A1 Jul. 14, 2011

(30) Foreign Application Priority Data
May 16, 2008 (EP) .................................... 08388017

(51) Int. Cl.
*A61L 9/00* (2006.01)
*A61L 9/015* (2006.01)
*A61L 9/20* (2006.01)
*A62B 7/08* (2006.01)
*B01D 53/00* (2006.01)
*B01J 19/00* (2006.01)

(52) U.S. Cl. .................. 422/4; 422/5; 422/24; 422/120; 422/121; 422/122; 422/123

(58) Field of Classification Search .................. 422/4, 5, 422/24, 120, 121, 122, 123
See application file for complete search history.

(56) References Cited

U.S. PATENT DOCUMENTS

| | | | | |
|---|---|---|---|---|
| 5,648,046 | A | 7/1997 | Weibel | |
| 6,589,486 | B1 | 7/2003 | Spanton | |
| 2004/0005252 | A1 | 1/2004 | Siess | |
| 2004/0120845 | A1 | 6/2004 | Potember et al. | |
| 2007/0140932 | A1 | 6/2007 | Bergeron et al. | |
| 2007/0181000 | A1 | 8/2007 | Wilson et al. | |
| 2009/0010801 | A1 * | 1/2009 | Murphy et al. | 422/4 |
| 2011/0274588 | A1 * | 11/2011 | Bergeron et al. | 422/121 |

FOREIGN PATENT DOCUMENTS

| | | | |
|---|---|---|---|
| GB | 2 302 004 | A | 12/1996 |
| WO | 2004/047877 | A2 | 6/2004 |
| WO | 2007/116130 | A1 | 10/2007 |
| WO | 2008/014540 | A1 | 2/2008 |

* cited by examiner

*Primary Examiner* — Timothy Vanoy
(74) *Attorney, Agent, or Firm* — Nath, Goldberg & Meyer; Jerald L. Meyer; Sanjana Mangalagiri

(57) ABSTRACT

A method and device for cleaning air. The air to be cleaned is directed as a continuous flow in succession through a) a first zone wherein the air is treated with ozone and possibly also water, ammonia or other aerosol growth promoters; b) a second zone wherein the air is subjected to ultraviolet light; c) a third zone wherein the air is maintained for a sufficient time to allow aerosol growth; d) a fourth zone where particles in the air are given an electrical charge; e) a fifth zone wherein the air is passed through an electrostatic filter; and f) a sixth zone wherein the air flows over a catalyst to break down residual ozone.

13 Claims, 1 Drawing Sheet

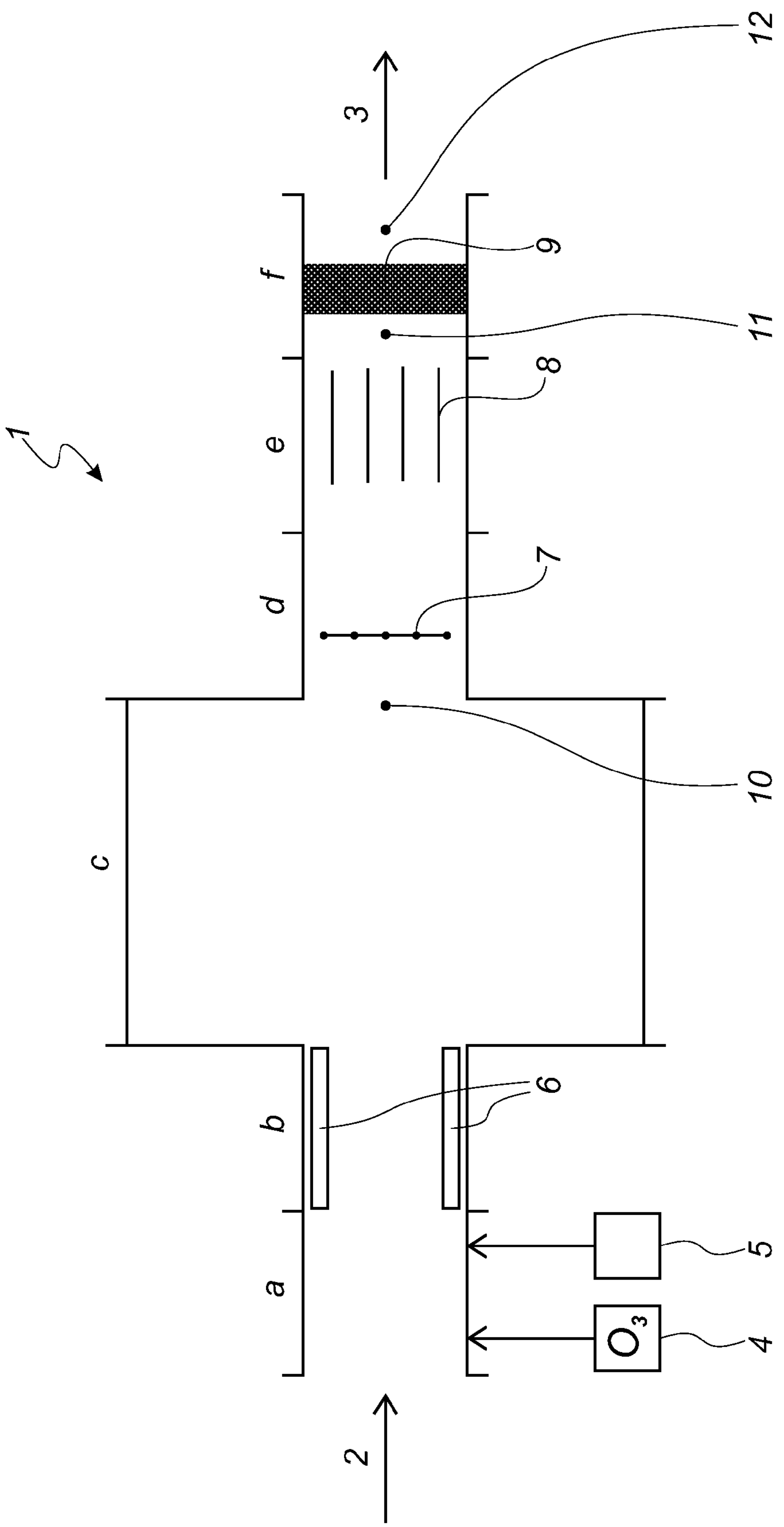
1
2
3
4
5
6
7
8
9
10
11
12
a
b
c
d
e
f
$O_3$

METHOD AND DEVICE FOR CLEANING AIR

This is a National Phase Application filed under 35 U.S.C. 371 as a national stage of PCT/EP2009/055849, filed May 14, 2009, an application claiming the benefit from European Patent Application No. 08388017.9, filed May 16, 2008, the content of each of which is hereby incorporated by reference in its entirety.

TECHNICAL FIELD

The present invention relates to a method and device for cleaning pollution from air wherein the air to be cleaned is subjected to a sequence of physical and chemical treatments.

BACKGROUND OF THE INVENTION

Indoor air pollution is produced by many sources including furniture and building materials, industrial activity, cooking and human metabolism. If nothing is done this pollution is detrimental to health and the quality of life. The main method for improving indoor air quality is dilution: fresh air is brought in from the outside. This is expensive because in a cold climate the air must be heated and in a warm climate it must be cooled and dehumidified.

Presently there is not a device available for cleaning large volumes of indoor air cheaply and efficiently. Mechanical filtration involves limited conductance and a pressure drop, necessitating large fans involving large energy consumption. In addition the filter must be changed and can itself become a source of bacteria. Electrostatic filtration does not cause a large pressure drop, but only removes pre-existing particles; it does not act on gas-phase pollution. Ozonolysis is used to remove odours but the chemical products of ozonolysis are often more hazardous than the original compounds, in addition there are important components of indoor air pollution that do not react with ozone. UV light is used to sterilize air in hospitals but this method removes only a very few specific types of pollution from the airstream.

U.S. Pat. No. 6,589,486 (Spanton) discloses an air purifying apparatus and method suitable for use in a standard forced air building Heating, Ventilating and/or Air Conditioning system (HVAC) of a building. The air is treated with ultraviolet (UV) radiation and ozone. The UV is germicidal and kills microorganisms, including both bacteria and viruses. The ozone cleans air and removes odours from air. Ozone in combination with UV radiation destroys microorganisms which are not killed by the UV radiation. Spanton does not disclose how to remove toxic gaseous contaminants and particles such as smoke and dust from the air. Thus Spanton does not suggest to control the process in order to optimize aerosol formation inter alia by ensuring a sufficient time to aerosol growth and/or by addition of aerosol formation accelerators such as water and ammonia.

US Patent Application 2004/0120845 (Potember et al.) discloses a method and apparatus for neutralizing airborne pathogens in ventilated air, and in heating or air conditioning systems. The system has a flow-through reaction chamber that contains a UV light source that emits short intense flashes of broad-spectrum UV light, a source of water vapour or spray, and an ozone generator. After the treatment with UV and ozone the air passes through a porous matrix and a solid support coated with an ozone removal catalyst. The passage through such matrix requires a sufficient pressure requiring substantial fan energy consumption. Furthermore Potember at al. do not disclose how to remove pollution from the air steam using the aerosol particle growth mechanism.

U.S. Pat. No. 5,656,242 (Morrow et al.) discloses an air purifier having a perforated plate between UV lamps and a porous air filter. Biological material is trapped by the filter and killed by the low dose of UV radiation which passes through the perforations in the plate. Filtered air passing through the plate is subjected to a high dose of UV radiation which sterilizes remaining biological material in the air. An electrostatic filter at the outlet may trap viruses which have been positively charged either by the action of the UV lamps or by positively charging the plate in order to strip electrons from the viruses. The UV lamps may be mercury lamps which are allowed to emit at both their ozone forming wavelength as well as the ozone breakdown wavelength. In such instance, a light filter surrounds the lamps which pass light only at the ozone breakdown wavelength. Air subjected to the unfiltered light is consequently exposed to ozone, which is a known biocide. The filtered light is in a zone which is filled with water mist such that hydroxyl radicals result. Air passing through this zone is scrubbed by the hydroxyl radicals. Morrow et al do not disclose how to treat the air with ozone before treatment with UV radiation. Morrow does not disclose removal of pollution via formation of aerosols. They do not control the dosage of ozone.

Electrostatic air purifiers are used to remove particles produced by welding. They are also marketed to clean indoor air, for example in offices and homes. These systems remove pre-existing particles (for example smoke), but do not remove toxic gases and other polluting compounds which are not in the form of particles.

Ozone is currently used to remove smells in many fields. Examples are kitchen exhaust, livestock barns and wastewater treatment plants. However the products of ozonolysis are typically more irritating and toxic than the original compounds so this is not a satisfactory solution as the air must be diluted substantially before it is safe to breathe.

UV light is used in air circulation systems of some hospitals to sterilize air. However, this application is not able to remove many types of pollution including most gas phase chemicals and particles.

The object of the present invention is to meet the demand of a universal or "broad-spectrum" removal of air pollution in an efficient and simple way with minimum energy consumption.

SUMMARY OF THE INVENTION

Accordingly, the present invention relates to a method for cleaning air wherein the air to be cleaned is directed as a continuous flow in succession through a) a first zone wherein the air is treated with ozone;
b) a second zone wherein the air is subjected to ultraviolet light;
c) a third zone wherein the air is maintained for a sufficient time to allow aerosol growth;
d) a fourth zone wherein particles in the air are provided with an electrical charge
e) a fifth zone wherein the air is passed through an electrostatic filter; and
f) a sixth zone wherein the air flows over a catalyst to break down residual ozone.

By "sufficient time to allow aerosol growth" as used herein, is meant a time in which a significant fraction of the actual pollution to be removed such as at least 60, 70 or 80% by weight, preferably 90% by weight, most preferably 99% by weight, of pollution which is able itself or whose reaction products are able to be removed by aerosol formation are removed from the airstream. In addition, pollution may be removed by concomitant photochemical processes, including ozonolysis, photolysis and radical reactions. The time required for aerosol formation may be dependent on the actual type and amount of pollution to be removed and can be estimated by the person skilled in the art based on relevant analyses. The required time may be ensured by proper design of the dimensions of the third zone (c) and/or the temperature in the third zone (c) and/or the airflow velocity in the third zone (c).

The present invention also relates to an air cleaning device including a channel with an air inlet for air to be cleaned and an air outlet for cleaned air and means for leading air through the channel from the inlet to the outlet wherein the channel has following zones in succession:

a) a first zone having a source of ozone;
b) a second zone having a source of ultraviolet light;
c) a third zone having a dimension which allows aerosol growth;
d) a fourth zone having an electrical discharge generator;
e) a fifth zone having one or more electrostatic filters; and
f) a sixth zone having a catalyst for removal of residual ozone.

The present invention provides a desirable "broad-spectrum" removal of the various types of indoor air pollution including irritating and/or toxic gases, organic compounds, microorganisms and liquid and solid particles being hazardous to health and detrimental to quality of life. Thus, the combined treatments not only kill microorganisms but also subject toxic and hazardous compounds to chemical reactions followed by agglomeration or capture of the resulting compounds together with small particles including dust and smoke in an aerosol growth zone resulting in aerosol particles sufficiently large to be removed from the air in an electrostatic filter after the aerosol particles have been electrically charged.

An advantage by the present inventive method is that the pressure drop through the device is relatively small whereby the energy consumption for the necessary air flow is low.

A further advantage is that the air can be cleaned sufficiently for reuse in larger and smaller rooms without or with a minimum of fresh air supply. Accordingly, it is possible to reduce the need for fresh air supply, and thereby reduce the energy required to heat or cool and dehumidify said fresh air. This makes the present invention suitable for use in rooms where access to fresh air is difficult or impossible.

In an embodiment of the inventive method the amount of ozone delivered into the first zone (a) is regulated through a feed-back system based on measurements by an ozone sensor situated in the third zone (c) and/or an ozone sensor situated in the fifth zone (e) and/or an ozone sensor situated in the sixth zone (f) which ozone sensor(s) ensure that no residual ozone escapes into the environment from the sixth zone (f).

Thus in one embodiment of the inventive method the amount of ozone delivered into the first zone (a) is regulated through a feed-back system based on measurements by an ozone sensor situated after the sixth zone (f) ensuring that no residual ozone escapes into the environment from the sixth zone.

To ensure a suitable amount of ozone in the first, second and third zones the amount of ozone delivered into the first zone (a) may be regulated through a feed-back system based on measurements by an ozone sensor situated in the third zone (c).

In a further embodiment the amount of ozone delivered into the first zone (a) may be regulated through a feed-back system based on combined measurements by ozone sensors after the sixth zone (f) and/or between the fifth (e) and the sixth (f) zone and/or in the third zone (c).

The electrical charge provided to the particles in the fourth zone (d) may be provided by a corona discharge or exposure to ionizing radiation from a radioactive source. The corona discharge is a simple, cheap and effective method for providing electrical charge to the particles.

Thus, in a preferred embodiment the electrical charge in the fourth zone (d) is provided by a corona discharge.

As explained above an important feature of the inventive method is the formation and growth of an aerosol. In case the air to be treated already contains sufficient moisture or other aerosol growth promoters further addition of such promoters may be unnecessary. However, depending on the air to be treated it is often preferred to add one or more aerosol growth promoters such as water and/or ammonia in the first zone (a).

Accordingly, the air cleaning device according to the invention preferably includes an injection system for the injection of ammonia and/or water vapour in the first zone (a).

A preferred catalyst for removal of residual ozone is manganese dioxide or cerium oxide.

The extent of applicability of the invention appears from the following detailed description. It should, however, be understood that the detailed description and the specific examples are merely included to illustrate the preferred embodiments and that various alterations and modifications within the scope of protection will be obvious to persons skilled in the art on the basis of the detailed description.

BRIEF DESCRIPTION OF THE DRAWING

The invention is explained in detail below with reference to the drawing, in which FIG. 1 is a schematic view of the inventive air cleaning device.

DETAILED DESCRIPTION OF THE INVENTION

The present invention relates to a method and device for removing pollution from air within a building ventilation system, air in a room or air in connection with a local source of pollution. In the following description, numerous specific details are set forth in order to provide a thorough understanding of the present invention. It will, however, be apparent to a person skilled in the art that the present invention may be practiced without these specific details.

One application of the present invention is to clean air in buildings, but a person skilled in the art would know that the method may equally well be used in other installations, such as without limitation, a small unit to clean air in a room or office, a train, an airplane or any other confined space with no or limited access to clean/fresh air. This small unit may or may not be portable.

To assure that all contaminated air enters and passes through the air cleaning system, the chamber air inlet and outlet may be adapted to fit the existing ducts using methods known in the art so that no air is allowed to bypass the system.

In one embodiment, the chamber air inlet/outlet is adapted to fit an existing HVAC air circulation system of, for example, a building.

FIG. 1 shows schematically an embodiment of the air cleaning device according to the invention arranged as a channel 1 with an inlet 2 for the air to be cleaned and an outlet 3 for the cleaned air. The airflow is provided with per se known means such as a fan (not shown). The inner side of the channel 1 comprises a first zone (a), a second zone (b) a third zone (c), a fourth zone (d), a fifth zone (e) and a sixth zone (f) placed successively in the airflow direction from left to right in FIG. 1.

A source of ozone 4 feeds ozone to the first zone (a) for ozone treatment of the air. Furthermore, the first zone (a) is optionally provided with one or more sources 5 of aerosol growth accelerators feeding water, ammonia and/or other aerosol growth accelerators into the first zone (a).

The next zone, the second zone (b), has a source of ultraviolet light for example UV lamps 6.

After the treatment first with ozone and then with UV radiation the air is maintained for sufficient time ensuring the desired chemical reactions including aerosol formation and growth in a third zone for aerosol growth (c). In the embodiment shown in FIG. 1 the necessary time is obtained by a broadening of the channel 1 giving a slower air velocity through the third zone (c). In an alternative embodiment the third zone (c) could be elongated using the same channel diameter throughout the zones (a)-(f).

The fourth zone (d) contains a source of electrical charge such as corona wires 7. By this means the solid and liquid particles in the aerosol as well as larger molecules will be electrically charged and caught in the fifth zone (e) containing an electrostatic filter element 8.

After the fifth zone (e) possible excess of ozone is removed from the air in the sixth zone (f) containing an ozone removal catalyst 9 where after the cleaned air leaves the channel 1 through the outlet 3.

To control the ozone treatment and ensure that the air leaving through the outlet 3 is substantially free of ozone, i.e. below the acceptable threshold limiting value, one or more ozone sensors are provided in the channel 1. Thus a first ozone sensor 10 may be placed near the end of the third zone (c), a second ozone sensor 11 may be placed between the fifth and sixth zones (e) and (f) and/or a third ozone sensor 12 after the sixth zone (f) at the outlet 3.

The amount of ozone provided by the ozone source 4 may be regulated through a feed-back system based on measurements by one or more of the sensors 10, 11 and 12.

The channel 1 can also be provided with one or more further sensors (not shown) for the measurement of other relevant conditions such as temperature, relative humidity and concentration of relevant contaminants. Together with the ozone measurements such measurements may be usable for regulation, control and monitoring purposes.

a) First Zone: Treatment with Ozone

In principle any source of ozone may be used in the treatment with ozone in the first zone provided the ozone can be delivered or generated in the desired amounts and in a safe way.

In a preferred embodiment the ozone source is an ozone generator as for example a corona discharge generator. While ozone can be generated using UV light, this is too inefficient and expensive at the present time. However, should the technology advance for generating ozone using UV or other methods, it may be incorporated into the present invention. Electric corona discharge generators produce large quantities of ozone in a short time. The passage of a high voltage, alternating electric current through an air stream containing oxygen breaks down molecular oxygen to atomic oxygen. These oxygen atoms may react to form ozone. Commercial ozone generators are available in various shapes and sizes with various capacities for generating ozone.

In another preferred embodiment the ozone source is an ozone generator from $O_3$ Technology which is based on a technology wherein oxygen or air is passed through parallel plates, and a charge is maintained by an AC voltage. The amount of ozone that enters the system is controlled by controlling the gas flow from this generator. This unit will produce the majority of the ozone in the system/reactor.

Ozone oxidizes aromatic- and unsaturated-hydrocarbons. However many kinds of compounds/chemicals, such as saturated hydrocarbons and material trapped in the liquid or solid phases of aerosols, do not react with ozone. Other indoor air pollutants that do not react with ozone include carbon monoxide and formaldehyde. Pollen and cigarette smoke react with ozone, but are not removed by ozonolysis.

The ozone acts as a biocide killing biological material, such as bacteria, moulds and the like in the air. Ozone is a naturally occurring substance which cleans air and removes odours from air.

The photochemical oxidation by $O_3$, OH and other species in the reaction region will mainly result in additional oxygen containing functional groups (e.g. alcohols, carbonyls, acids, etc.) on organic pollution molecules. Each functional group will reduce the vapour pressure of the organic molecule increasing its propensity for forming aerosols.

The first zone may in addition to an ozone source also, optionally, contain an injection system, i.e. a water source, for the introduction of water vapour (which also includes humid air), or small water droplets and the step of introducing ozone to the zone is performed by forming either a mixture of water vapour and/or water droplets and ozone before introducing the mixture into the zone.

A further, optional, addition may comprise an injection system for the introduction of ammonia, i.e. an ammonia source.

Addition of water or ammonia promotes aerosol formation.

The dimensions of the first zone should be designed to ensure the necessary treatment time t1 in the zone defined as the time from the point where the air contacts the ozone to the point immediately before it is subjected to UV. The necessary time t1 depends on various factors including the type of contamination, the ozone source and the temperature. Based on the required flow rates in an HVAC system and the dimensions, t1 should typically be less than 15 seconds, preferably less than 10 seconds, such as less than 8 seconds. Typically t1 should be above 1 second, preferably above 5 seconds.

b) Second Zone: Irradiation with Ultraviolet Light

The ultraviolet light source used in the second zone may be any conventional source providing UV-C light. Such UV-C light is per se a biocide because it denatures DNA.

Broad-spectrum ultraviolet light with a wavelength between 100 and 330 nm causes ozone and water to react forming highly reactive ozone-based free radical intermediates, such as hydroxyl radicals, that in turn react with and neutralize airborne pathogens.

UV-C light initially breaks down the ozone, exiting from the first zone, into oxygen ($O_2$) and an electronically excited oxygen atom (O*) also termed an oxygen radical.

In the presence of water this excited oxygen radical may react with water (moisture) in the air and form hydroxyl radicals:

$$O^*+H_2O \rightarrow 2.OH$$

Furthermore, the excited oxygen radical may react with a hydrocarbon or with an oxygen molecule to reform ozone:

$$O_3+h\nu \rightarrow O_2+O^*$$

$$O^*+H_2O \rightarrow 2.OH$$

$$O^*+RH \rightarrow OH+.R$$

$$O^*+M \rightarrow O+M$$

$$O+O_2+M \rightarrow O_3+M$$

where hν is photon with a wavelength below 330 nm,

.OH is a hydroxyl radical,

RH is a hydrocarbon and

M is a collision partner, usually $N_2$ or $O_2$.

Hydrocarbon radicals (.R) may react by addition or fragmentation to obtain aldehydes, ketones, acids, alcohols or other functionalised hydrocarbons.

Thus in the second zone, some of the ozone will be broken down into oxygen gas and hydroxyl radicals. It will also be recognised by those skilled in the art that hydroxyl radicals can also form peroxides, which themselves can act as biocides. Therefore, these peroxides, in addition to the hydroxyl radicals, assist in killing any living biological material which may enter the zone.

Hydrocarbons may react with hydroxyl radicals:

$$CH_4+.OH \rightarrow .CH_3+H_2O$$

$$.CH_3+O_2+M \rightarrow .CH_3O_2+M$$

$$.CH_3O_2+NO \rightarrow .CH_3O+NO_2$$

$$.CH_3O+O_2 \rightarrow CH_2O+.HO_2$$

NO is present in the background air. Any kind of hydrocarbon will make an oxy radical like the methoxy radical above, and this radical can donate an H to $O_2$ to form a stable aldehyde/ketone and $.HO_2$. Another source of $H_2O_2$ will be:

$$.HO_2+.HO_2 \rightarrow H_2O_2+O_2$$

Ozone in combination with UV radiation, which may form hydroxyl radicals and/or peroxides, destroys microorganisms which are not killed by the UV radiation as such.

The free radicals formed by the interaction of ozone with water in the presence of UV light, act as oxidants on cell walls even before they penetrate inside the microorganisms where they oxidize essential components such as enzymes and proteins.

Ozone does not itself react significantly with either water or oxygen in the absence of UV irradiation. Water and air merely provide the medium in which ozone diffuses to react with organic molecules such as those on the outside of the cell wall of pathogens such as bacteria, viruses, moulds or pollen. UV irradiation causes ozone to react with water and to decompose into various highly reactive free radicals, such as hydroxyl radicals.

The dimensions of the second zone should be designed to ensure the necessary treatment time t2 in this zone defined as the time from the point where the air it is subjected to UV to the point where it leaves the UV radiation. The required time t2 depends on various factors including the type of contamination, the treatment in the first zone, the UV radiation source and the temperature. Typically t2 should be less than five minutes, preferably less than 10 seconds, such as less than 8 seconds. Typically t2 should be longer than 50 ms, preferably above 0.1 second, such as above 5 seconds.

t2 should be relatively long time as carbon monoxide reacts rather slowly with OH, in order to remove it a treatment time of up to five minutes may be needed.

c) Third Zone: Aerosol Growth

An important feature of the inventive method is that an aerosol growth zone is provided after the second zone of UV treatment. The purpose of this zone is to allow particles to grow, removing pollution from the gas phase. One problem by prior art air purification is that smells of cooking oil and diesel or heating oil cannot be removed, even by ozone. Due to the use and formation of .OH, other radicals derived from ozone or other sources, and aerosols these pollutants can be removed by the inventive method.

The aerosol growth chamber may involve increasing the cross sectional area of the flow duct in order to decrease the flow rate, allowing time for the aerosols to grow.

Accordingly, the dimensions of the third zone should be designed to ensure the necessary retention time t3 in this zone defined as the time from the point where the air leaves the second zone of UV radiation to the point immediately before it enters into the electrostatic filter in the fourth zone. The necessary time t3 depends on various factors including the type of contamination, the treatments in the first and second zones, and the temperature. Typically t3 should be less than five minutes, preferably less than 10 seconds, such as less than 8 seconds. Typically t3 should be longer than 50 ms, preferably above 0.1 second, such as above 5 seconds.

d) Fourth Zone: Electrical Charge

In the fourth zone the air leaving the second zone is subjected to a source providing the molecules, particles and droplets with an electrical charge enabling removal thereof with an electrostatic filter in the following zone. In a preferred embodiment the source of electrical charge is a corona discharge.

A small, negligible, amount of ozone is produced by the corona discharge wires. However, this is a by-product and it contributes only a minor amount of the total ozone.

The corona discharge in the fourth zone gives an electrical charge to particles in the airstream allowing them to be removed by the electrostatic filter in the fifth zone.

It is possible that charging the particles will improve aerosol particle trapping because the agglomeration of oppositely charged particles will increase particle size, and the presence of charge will improve the thermodynamics of particle growth.

Heavier combined particles may precipitate (fall) out of the air when two smaller particles agglomerate.

The dimensions of the fourth zone should be designed to ensure the necessary treatment time t4 in this zone defined as the time from the point where the air it is subjected to an electrical charge to the point immediately before it enters into the electrostatic filter. The necessary time t4 depends on various factors including the type of contamination, the treatments in the first and second zones, the source of the electrical charge and the temperature. This time need not be long. The requirement is that the aerosols are charged before the electrostatic filter in the fifth zone, and this is a fast process. In most cases t4 should be between 0.01 and 2 seconds, preferably 0.05-1.0 seconds, such as 0.1-0.8 second.

e) Fifth Zone: Passage Through Electrostatic Filter

Any electrostatic precipitator can be used in the present invention. An electrostatic precipitator is a particulate collection device that removes particles from a flowing gas (such as air) using the force of an induced electrostatic charge. Electrostatic precipitators are highly efficient filtration devices that minimally impede the flow of gases through the zone, and can efficiently remove fine particulate matter such as smoke or dust from the air stream.

Smaller particles, which are not heavy enough to precipitate, are forced out through electrostatic filtration. The electrostatic filtration comprises charged metal plates, with alternating positive and negative charges, where positive aerosol-particles will accelerate into the negative plates and negative aerosol-particles will accelerate into the positive plates.

The addition of moisture, ammonia and/or other agents to the incoming air improves the efficiency of trapping pollution and pollution oxidation products through the mechanism of aerosol growth.

The dimensions of the fifth zone should be designed to ensure the necessary treatment time t5 in this zone defined as the time from the point where the air enters into the electrostatic filter to the point immediately before it contacts the catalyst for removal of residual ozone. The necessary time t5 depends on various factors including the type of contamination, the treatments and reactions in the first, second, third and fourth zones, the type of electrostatic filter and the temperature. Generally this time need not be long.

f) Sixth Zone: Removal of Residual Ozone

A catalyst for removal of residual ozone is essential for the present invention, since prolonged exposure to elevated concentrations of ozone may irritate the respiratory system and harm the lungs. The U.S. Environmental Protection Agency classifies average 8-hour exposures of 85 to 105 parts per billion as unhealthy for sensitive groups. Concentrations higher than this increase the risks.

To ensure that no harmful residual ozone will contaminate the air that exits the sixth zone, one or more ozone removal catalysts known in the art may be placed in that zone. Ozone removal catalysts that can be used in various embodiments include, manganese dioxide, all-aluminium catalyst, a carbon-supported metal oxide, copper chloride-coated carbon fibres, carbon-iron aerosol particles, and metal catalysts. CARULITE® (an inorganic oxide) made by Carus Chemical Company is another ozone removal catalyst. The catalyst may be solid-supported, and any solid support may be used, especially glass or silica which substances can catalyze ozone decomposition. The catalyst could also comprise manganese dioxide containing paint.

The catalyst for removal of residual ozone will have a large surface area for contacting the air containing the residual ozone. The sixth zone should also have a minimum pressure drop. To this end the catalyst material may be applied in the shape of a honeycomb (hexagonal shape).

The unstable and highly reactive free radical intermediates obtained from ozone, e.g. hydroxyl radicals, form stable products including water and carbon dioxide that are not associated with health risks when present in air at small concentrations. The decomposition of ozone into stable oxygen is accelerated by surfaces that act as substrates and/or reaction-sites for the decomposition process.

Feed-Back System/Ozone Sensors:

The device will be equipped with ozone sensors for safety and efficient control. For example an ozone sensor in the aerosol growth chamber (third zone) would help to control ozone dosage in response to changing pollution levels, and a sensor at the exit of the device will ensure the overall safe operation.

Examples of the chemical and/or physical reactions believed to occur during the inventive method include:

A. Unsaturated (including aromatic) hydrocarbons, for example benzene and isoprene, react directly with ozone in the first zone (a) where ozone is added, or with ozone found later in the system for example in the aerosol growth chamber of third zone (c). In principle, the reaction with ozone could take place anywhere where ozone is present that is from the first zone (a) where ozone is added until it is removed by the catalyst in the sixth zone (f).

B. Saturated hydrocarbons including small species such as methane or propane and larger molecules such as diesel or cooking oil, and some other species including carbon monoxide and formaldehyde will react with the hydroxyl radical .OH or other ozone-based radicals formed when $O_3$ is photolysed by the UV lamps in the presence of water vapour.

C. The products of the reactions of type A and B will typically condense onto aerosol particles, either pre-existing particles or newly nucleated particles. (Sometimes however the products will include volatile species as $CO_2$ that are less polluting than the precursors). All particles will be removed from the airstream by the electrostatic filter.

The present invention can be applicable in a variety of places such as, but not limited to:

1) cleaning air in buildings or rooms, for example offices, kitchens and apartments, to improve air quality and reduce cost of bringing in fresh air;
2) cleaning air in airplanes or other vehicles having confined spaces with no or limited access to fresh/clean air which would reduce disease transmission, reduce amount of fresh air brought in from outside;
3) provide clean air for people with allergies to chemicals or particles;
4) providing clean sterile air in hospitals; and
5) at point sources of air pollution, to remove for example oil used as part of a manufacturing process or fuel oil/diesel fumes.

In the foregoing description, the invention has been described with reference to specific embodiments thereof. It will, however be evident that various modifications and changes may be made to the invention without departing from the broader scope of the present invention. The present application will be described in further detail, by the following non-limiting examples.

EXAMPLES

Example 1

In a building with a total volume of free space of 60.000 $m^3$ and provided with a standard Heating, Ventilating and/or Air Conditioning system (HVAC) the air cleaning device as described in FIG. 1 is installed in the HVAC system. The air flow through of the device is 7200 $m^3$/h giving a flow velocity of 5 m/s in the first and second zones ensuring the required treatment times in the first, second, fourth and fifth zones.

The ozone source in the first zone provides 200 g/h ozone giving an ozone concentration of 14 ppm inside the device.

The outlet air, in comparison to the inlet air, shows significantly reduced concentrations of several classes of pollution including particles, scents including perfumes, hydrocarbons, volatile organic compounds, carbon monoxide and formaldehyde.

Example 2

The air cleaning system described in FIG. 1 is installed in an office, apartment, hospital room, kitchen or other smaller room with a volume of roughly 100 cubic meters. A freestanding enclosed air cleaning unit as described in FIG. 1 including a fan is placed in the room. It has a flow rate of 2 m/s and cross section of 0.02 square meters giving a flow rate of 0.04 cubic meters per second, meaning that on average air will circulate through the device every 40 minutes. The device can be used to eliminate air pollution from the room, including volatile chemicals, smoke, odours and allergens.

Example 3

The air cleaning system described in FIG. 1 is used to treat air from a local source of pollution, for example oil vapours given off by the cutting tool of a lathe or mill, in association with use of diesel or heating oil in a building, or when solvents are used for painting or gluing. The air from the process is drawn through the device by a fan and the pollution is prevented from entering the rest of the room or building.

The above description of the invention reveals that it is obvious that it can be varied in many ways. Such variations are not to be considered a deviation from the scope of the invention, and all such modifications which are obvious to persons skilled in the art are also to be considered comprised by the scope of the succeeding claims.

The invention claimed is:

1. A method for cleaning air wherein the air to be cleaned is directed as a continuous flow in succession through a) a first zone wherein the air is treated with ozone;

b) a second zone wherein the air is subjected to ultraviolet light;

c) a third zone wherein the air is maintained for a sufficient time to allow aerosol growth;

d) a fourth zone wherein particles in the air are provided with an electrical charge;

e) a fifth zone wherein the air is passed through an electrostatic filter; and f) a sixth zone wherein the air flow over a catalyst to break down residual ozone.

2. The method according to claim 1 wherein the air in the first zone (a) further is treated with water and/or ammonia and/or other aerosol promoters.

3. The method according to claim 1 wherein airstream pollution is converted into aerosols by oxidation with ozone or ozone-based radicals and by controlling the temperature and/or the electrical charge and/or the addition of aerosol growth promoters.

4. The method according to claim 1 wherein the amount of ozone delivered into the first zone (a) is regulated through a feed-back system based on measurements by an ozone sensor situated in the third zone (c) and/or an ozone sensor situated in the fifth zone (e) and/or an ozone sensor situated in the sixth zone(f) which ozone sensor(s) ensure that no residual ozone escapes into the environment from the sixth zone (f).

5. The method according to claim 1, wherein the electrical charge in the fourth zone (d) is provided by a corona discharge.

6. An air clean device including a channel with an air inlet for air to be cleaned and an air outlet for cleaned air and means for leading air through the channel from the inlet to the outlet wherein the channel has following zones in succession:

a) a first zone having a source of ozone;

b) a second zone having a source of ultraviolet light;

c) a third zone having a dimension which allows time for aerosol growth;

d) a fourth zone having an electrical discharge generator;

e) a fifth zone having one or more electrostatic filters; and f) a sixth zone having a catalyst for removal of residual ozone.

7. The air cleaning device according to claim 6, wherein the first zone (a) further includes an injection system for the injection of ammonia and/or water vapor.

8. The air cleaning device according to claim 7 wherein the amount of ozone delivered into the first zone (a) is regulated through a feed-back system based on measurements by an ozone sensor situated in the third zone (c) and/or an ozone sensor situated between the fifth zone (e) and the sixth zone (f) and/or an ozone sensor situated in the sixth zone (f) after the catalyst.

9. The air cleaning device according to claim 8 comprising an ozone sensor placed after the sixth zone (f) and optionally an ozone sensor between the fifth zone (e) and the sixth zone (f).

10. The air cleaning device according to claim 8 further comprising a feed-back system for regulation of ozone formation according to the amount of ozone detected by one of the ozone sensors and optionally combined with to the amount of ozone detected by one or more of the further ozone sensors.

11. The air cleaning device of claim 6 wherein the catalyst for removal of residual ozone is manganese dioxide or cerium oxide.

12. Use of the air cleaning device according to claim 6 for the cleaning of air.

13. The use according to claim 12 for cleaning air in buildings and rooms to improve air quality and reduce cost of bringing in fresh air; cleaning air in airplanes or other vehicles having confined spaces with no or limited access to fresh/clean air; cleaning air for people with allergies to chemicals or particles; for providing clean sterile air in hospitals; for cleaning air at point sources of air pollution; or to remove oil used as part of a manufacturing process or fuel oil/diesel fumes.

* * * * *